US008053424B2

(12) United States Patent
Miller et al.

(10) Patent No.: US 8,053,424 B2
(45) Date of Patent: Nov. 8, 2011

(54) COMPOSITION AND METHOD OF TREATING HEARING LOSS

(75) Inventors: Josef Miller, Ann Arbor, MI (US); Colleen Garbe-LePrell, Ypsilanti, MI (US); Daisuke Yamashita, Yokohama (JP)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 12/839,245

(22) Filed: Jul. 19, 2010

(65) Prior Publication Data

US 2010/0305075 A1 Dec. 2, 2010

Related U.S. Application Data

(62) Division of application No. 11/384,579, filed on Mar. 20, 2006, now Pat. No. 7,786,100.

(51) Int. Cl.
*A61K 31/60* (2006.01)
*A61P 27/16* (2006.01)
(52) U.S. Cl. ................. 514/161; 514/159; 514/458
(58) Field of Classification Search ............ 514/159, 514/458, 164, 161
See application file for complete search history.

(56) References Cited

U.S. PATENT DOCUMENTS

| | | | |
|---|---|---|---|
| 6,093,417 | A | 7/2000 | Petrus |
| 6,423,321 | B2 | 7/2002 | Tobinick |
| 6,524,619 | B2 | 2/2003 | Pearson et al. |
| 6,660,297 | B2 | 12/2003 | Bartels et al. |
| 2003/0191064 | A1 | 10/2003 | Kopke |
| 2004/0033273 | A1* | 2/2004 | Patwardhan et al. ......... 424/725 |
| 2004/0101560 | A1 | 5/2004 | Sawchuk et al. |
| 2004/0247570 | A1 | 12/2004 | Miller et al. |
| 2005/0013854 | A1 | 1/2005 | Mannino et al. |
| 2005/0070607 | A1 | 3/2005 | Andrus et al. |
| 2005/0107338 | A1 | 5/2005 | Seidman |

OTHER PUBLICATIONS

Ahn et al., Anti-Apoptotic Role of Retinoic Acid in the Inner Ear of Noise-Exposed Mice, Biochemical and Biophysical Research Commmunications 335 (2005) 485-490.
Abaamrane et al., "Long-term Administration of Magnesium After Acoustic Trauma Caused by Gunshot Noise in Guinea Pigs", Hearing Research 247, 2009, pp. 137-145.
Attias, J., Bresloff, I., Haupt, H., Scheibe, F., Ising, H. (2003). "Preventing noise induced otoacoustic emission loss by increasing magnesium (Mg2+) intake in guinea-pigs." J. Basic Clin. Physiol. Pharmacol. 14, 119-136.
Attias, J., Weisz, G., Almog, S., Shahar, A., Wiener, M., Joachims, Z., Netzer, A., Ising, H., Rebentisch, E., Guenther, T. (1994). Oral magnesium intake reduces permanent hearing loss induced by noise exposure. Am. J. Otolaryngol. 15, 26-32.
Attias et al., "Reduction in Noise-Induced Temporary Threshold Shift in Humans Following Oral Magnesium Intake", Clinical Otolaryngology 29, Blackwell Publishing Ltd, 2004, pp. 635-641.
Balavoine GG, Geletii YV (1999) Peroxynitrite scavenging by different antioxidants. Part I: Convenient Assay. Nitric Oxide 3:40-54.
Bertolaso, L, Martini, A., Bindini, D., Lanzoni, I., Parmeggiani, A., Vitali, C., Kalinec, G., Kalinec, E, Capitani, S., Previati, M. (2001). Apoptosis in the OC-k3 immortalized cell line treated with different agents. Audiology 40, 327-35.
Biesalski, H. K., Wellner, U., Weiser, H. (1990). Vitamin A deficiency increases noise susceptibility in guinea pigs. J. Nutr. 120, 726-37.
Boland A, Gerardy J, Mossay D, Seutin V (2003) Pre- and posttreatment with pirlindole and dehydropirlindole protects cultured brain cells against nitric oxide-induced death. Eur J Pharmacol 466:21-30.
Branis et al., "Effect of Ascorbic Acid on the Numerical Hair Cell Loss in Noise Exposed Guinea Pigs", Hearing Research 33, Elsevier Science Publishers B.V., 1988, pp. 137-140.
Cevette, M. J., Vormann, J., Franz, K. (2003). Magnesium and hearing. J. Am. Acad. Audiol. 14, 202-12.
Chae HJ, Chae SW, Reed JC, Kim HR (2004) Salicylate regulates COX-2 expression through ERK and subsequent NF-kappaB activation in osteoblasts. Immunopharmacol Immunotoxicol 26:75-91.
Diamond, B. J., Shiflett, S. C., Feiwel, N., Matheis, R. J., Noskin, O., Richards, J. A., Schoenberger, N. E. (2000). Ginkgo biloba extract: mechanisms and clinical indications. Arch. Phys. Med. Rehabil. 81, 668-78.
Didier, A., Droy-Lefaix, M. T., Aurousseau, C., Cazals, Y. (1996). Effects of Ginkgo biloba extract (EGb 761) on cochlear vasculature in the guinea pig: morphometric measurements and laser Doppler flowmetry. Eur. Arch. Otorhinolaryngol. 253, 25-30.
Duan, M., Qiu, J., Laurell, G., Olofsson, A., Counter, S. A., Borg, E. (2004). Dose and time-dependent protection of the antioxidant N-Lacetylcysteine against impulse noise trauma. Hear. Res. 192, 1-9.
Evans, P., Halliwell, B. (1999). Free radicals and hearing. Cause, consequence, and criteria. Ann. N.Y. Acad. Sci. 884, 19-40.

(Continued)

*Primary Examiner* — Sreeni Padmanabhan
*Assistant Examiner* — Sahar Javanmard
(74) *Attorney, Agent, or Firm* — Howard & Howard Attorneys PLLC (57) ABSTRACT

A composition for treating hearing loss includes components that function through different biological mechanisms to provide an additive effect that is greater than the effect of the individual components alone. The composition includes a biologically effective amount of vitamin E for inhibiting propagation of lipid peroxidation that contributes to hearing loss. The composition also includes a biologically effective amount of a salicylate for reducing hydroxyl radicals that contribute to hearing loss. A method of treating hearing loss includes the step of internally administering the composition, as described above, to a mammal within three days of trauma to a middle or inner ear of the mammal. In other words, the composition is effective even when administered as late as three days after trauma to a middle or inner ear of a mammal.

7 Claims, 4 Drawing Sheets

OTHER PUBLICATIONS

Fetoni AR, Sergi B, Ferraresi A, Paludetti G, Troiani D (2004) alpha-Tocopherol protective effects on gentamicin ototoxicity: an experimental study. Int J Audiol 43:166-171.

Fischer et al., "Protection Of the Cochlea by Ascorbic Acid in Noise Trauma", HNO 57(4), Apr. 2009, pp. 339-344.

English language abstract for Fischer et al., "Protection Of the Cochlea by Ascorbic Acid in Noise Trauma", HNO 57 (4), Apr. 2009, pp. 339-344.

Floyd RA (1999) Antioxidants, oxidative stress, and degenerative neurological disorders. Proc Soc Exp Biol Med 222:236-245.

Gordin, A., Goldenberg, D., Golz, A., Netzer, A., Joachims, H. Z. (2002). Magnesium: a new therapy for idiopathic sudden sensorineural hearing loss. Otol. Neurotol. 23, 447-51.

Gunther, T., Ising, H., Joachims, Z. (1989). Biochemical mechanisms affecting susceptibility to noise-induced hearing loss. Am. J. Otol. 10, 36-41.

Gutteridge, J. M. C., Halliwell, B. 1999. Antioxidant protection and oxygen radical signaling. In: Gilbert, D.L, Colton, C. A., (Eds.), Reactive oxygen species in biological systems: An interdisciplinary approach. Kluwer Academic/Plenum Publishers, New York. pp. 189-218.

Halliwell, B, Gutteridge, J.M.C., Free Radicals in Biology and Medicine, 3rd Ed., Oxford Univ. Press (1999), Chapter 3—Antioxidant defences, pp. 105-245.

Haupt, H. Scheibe, F. (2002). Preventive magnesium supplement protects the inner ear against noise-induced impairment of blood flow and oxygenation in the guinea pig. Magnes. Res. 15, 17-25.

Haupt, H., Scheibe, F., Mazurek, B. (2003). Therapeutic efficacy of magnesium in acoustic trauma in the guinea pig. ORL. J. Otorhinolaryngol. Relat. Spec. 65, 134-9.

Heinrich et al, "Ascorbic Acid Reduces Noise-Induced Nitric Oxide Production in the Guinea Pig Ear", Laryngoscope 118, The American Laryngological, Rhinological and Otological Society, Inc., May 2008, pp. 837-842.

Henderson, D., McFadden, S. L., Liu, C. C., Hight, N., Zheng, X. Y. (1999). The role of antioxidants in protection from impulse noise. Ann. N. Y. Acad. Sci. 884, 368-80.

Hight, N. G., McFadden, S. L., Henderson, D., Burkard, R. F., Nicotera, T. (2003). Noise-induced hearing loss in chinchillas pretreated with glutathione monoethylester and R-PIA. Hear. Res. 179, 21-32.

Hou, F., Wang, S., Zhai, S., Hu, Y., Yang, W., He, L. (2003). Effects of alpha-tocopherol on noise-induced hearing loss in guinea pigs. Hear. Res. 179, 1-8.

Hu, B. H., Zheng, X. Y., McFadden, S. L., Kopke, R. D., Henderson, D. (1997). R-phenylisopropyladenosine attenuates noise-induced hearing loss in the chinchilla. Hear. Res. 113, 198-206.

Ising, H., Handrock, M., Gunther, T., Fischer, R., Dombrowski, M. (1982). Increased noise trauma in guinea pigs through magnesium deficiency. Arch. Otorhinolaryngol. 236, 139-46.

Jackson, R. L., Coleman, J. K, Ge, X., Liu, J., Hoffer, M. E., Balough, B. (2005). Antioxidant strategies for post-noise hearing loss recovery, International Symposium—Pharmacologic Strategies for Prevention and Treatment of Hearing Loss and Tinnitus, Niagra Falls, Ottawa, Canada, one page.

Jacono A.A., Hu B, Kopke RD, Henderson D, Van De Water TR, Steinman HM (1998) Changes in cochlear antioxidant enzyme activity after sound conditioning and noise exposure in the chinchilla. Hear Res 117:31-38.

Joachims, H. Z., Segal, J., Golz, A., Netzer, A., Goldenberg, D. (2003). Antioxidants in treatment of idiopathic sudden hearing loss. Otol. Neurotol. 24, 572-5.

Joachims, Z., Babisch, W., Ising, H., Gunther, T., Handrock, M. (1983). Dependence of noise-induced hearing loss upon perilymph magnesium concentration. J. Acoust. Soc. Am. 74, 104-8.

Joachims, Z., Netzer, A., Ising, H., Rebentisch, E., Attias, J., Weisz, G., Gunther, T. (1993). Oral magnesium supplementation as prophylaxis for noise-induced hearing loss: results of a double blind field study. Schriftenr. Ver. Wasser. Boden. Lufthyg. 88, 511-516.

Jung, H. W., Chang, S. O., Kim, C. S., Rhee, C. S., Lim, D. H. (1998). Effects of Ginkgo biloba extract on the cochlear damage induced by local gentamicin installation in guinea pigs. J. Korean Med. Sci. 13, 525-8.

Kalkanis, J. G., Whitworth, C., Rybak, L. P. (2004). Vitamin E reduces cisplatin ototoxicity. Laryngoscope 114, 538-42.

Knight, W. 2002. Popping pill may prevent hearing loss [Online] http://www.newscientist.com/article.ns?id=dn2666 (posted Aug. 13, 2002; verified Feb. 25, 2005) on 2 pages.

Kopke, R. D. (2005). NAC for Noise: From the bench top to the clinic, International Symposium—Pharmacologic Strategies for Prevention and Treatment of Hearing Loss and Tinnitus, Niagra Falls, Ottawa, Canada, one page.

Kopke, R. D. Coleman, J. K., Liu, J., Campbell, K. C., Riffenburgh, R. H. (2002). Candidate's thesis: Enhancing intrinsic cochlear stress defenses to reduce noise-induced hearing loss. Laryngoscope 112, 1515-32.

Kopke, R. D., Weisskopf, P. A., Boone, J. L., Jackson, R. L., Wester, D. C., Hoffer, M. E., Lambert, D. C., Charon, C. C., Ding, D. L., McBride, D. (2000). Reduction of noise-induced hearing loss using L-NAC and salicylate in the chinchilla. Hear. Res. 149, 138-46.

Kopke R, Allen KA, Henderson D, Hoffer M, Frenz D, Van de Water T(1999) A radical demise. Toxins and trauma share common pathways in hair cell death. Ann N Y Acad Sci 884:171-191.

Kujawa S.G., Liberman M.C., Acceleration of Age-Related Hearing Loss by Early Noise Exposure: Evidence of a Misspent Youth, Journal of Neuro., (Feb. 15, 2006—26(7): 2115-2123.

Kujawa, S. (2005). Adding insult to injury: Noise-induced and age-related hearing loss interactions, International Symposium—Pharmacologic Strategies for Prevention and Treatment of Hearing Loss and Tinnitus, Niagra Falls, Ottawa, Canada, one page.

Kwon KS, Chae HJ (2003) Sodium salicylate inhibits expression of COX-2 through suppression of ERK and subsequent NF-kappaB activation in rat ventricular cardiomyocytes. Arch Pharm Res 26:545-553.

Laurikainen et al., "Betahistine Effects on Cochlear Blood Flow: From the Laboratory to the Clinic", Acta Otolaryngol, Supp. 544, 2000, pp. 5-7.

Laurikainen et al., "Non-Specific Effect of Beettahistine on Cochlear Electrophysiology in Guinea Pig", Acta Otolayngol (Stockh), Supp. 529, 1997, pp. 77-79.

Le Prell et al., "Free Radical Scavengers Vitamins A, C and E Plus Magnesium Reduce Noise Trauma", Free Radical Biology & Medicine 42, 2007, pp. 1454-1463.

Le Prell et al., "Mechanisms of Noise-Induced Hearing Loss Indicate Multiple Methods of Prevention", Hearing Research 226, Elsevier B.V., 2007, pp. 22-43.

Le Prell CG, Dolan DF, Schacht J, Miller JM, Lomax MI, Altschuler RA (2003) Pathways for protection from noise induced hearing loss. Noise Health 5:1-17.

Li G, Sha SH, Zotova E, Arezzo J, Van de Water T, Schacht J (2002) Salicylate protects hearing and kidney function from cisplatin toxicity without compromising its oncolytic action. Lab Invest 82:585-596.

Lohle, E. (1980). The influence of a chronic vitamin A deficiency on the acoustic sensory cells and the ganglion spirale cochleae of the rat. An electron microscope study. Arch. Otorhinolaryngol. 229, 45-53.

Lohle, E. (1985). Ultrastructural changes in the organ of Corti and in the ganglion spiral cochleae after vitamin A deficiency. Pathol. Res. Pract. 179, 560-7.

Lopez-Gonzalez, M. A., Guerrero, J. M., Rojas, F., Delgado, F. (2000). Ototoxicity caused by cisplatin is ameliorated by melatonin and other antioxidants. J. Pineal Res. 28, 73-80.

McFadden, S.L., Wo, J.M., Michalak, N. Ding D., Dietary Vitamin C Supplementation Reduces Noise-Induced Hearing Loss in Guinea Pigs, Hearing Research 202 (2005) 200-208.

Miller et al., "Interactive Effects of Aging with Noise Induced Hearing Loss", Scand. Audiol, 27, 1998, pp. 53-61.

Miller et al., "Mechanisms and Prevention of Noise-Induced Hearling Loss", Otol Jpn, 16(2): 2006, pp. 139-1.

Miller, J. M., Brown, J. N., Schacht, J. (2003). 8-iso-prostaglandin F(2alpha), a product of noise exposure, reduces inner ear blood flow. Audiol. Neurootol. 8, 207-21.

Minami et al., "Creatine and Tempol Attenuate Noise-Induced Hearing Loss", Brain Res. May 7, 2007, pp. 1-13.

Nageris, B. I., Ulanovski, D., Attias, J. (2004). Magnesium treatment for sudden hearing loss. Ann. Otol. Rhinol. Laryngol. 113, 672-5.

Ohinata, Y., Miller, J. M., Schacht, J. (2003). Protection from noise-induced lipid peroxidation and hair cell loss in the cochlea. Brain Res. 966, 265-73.

Ohinata, Y., Miller, J. M., Altschuler, R. A., Schacht, J. (2000a). Intense noise induces formation of vasoactive lipid peroxidation products in the cochlea. Brain Res. 878, 163-73.

Ohinata, Y., Yamasoba, T., Schacht, J., Miller, J. M. (2000b). Glutathione limits noise-induced hearing loss. Hear. Res. 146, 28-34.

Omenn, G. S., Goodman, G. E., Thornquist, M. D., Balmes, J., Cullen, M. R., Glass, A., Keogh, J. P., Meyskens, F. L., Valanis, B., Williams, J. H., Barnhart, S., Hammar, S. (1996). Effects of a combination of beta carotene and vitamin A on lung cancer and cardiovascular disease. N. Engl. J. Med. 334, 1150-5.

Perlman, H. B., Kimura, R. (1962). Cochlear blood flow and acoustic trauma. Acta Otolaryngol. (Stockh). 54, 99-119.

Rabinowitz, P. M., Pierce Wise, J., Sr., Hur Mobo, B., Antonucci, P. G., Powell, C., Slade, M. (2002). Antioxidant status and hearing function in noise-exposed workers. Hear. Res. 173, 164-71.

Romeo, G. (1985) The Therapeutic Effect of Vitamins A and E in Neurosensory Hearing Loss, [Italian] Journal Article—Acta Vitamininol. Enzymol. 7 Suppl:85-92, One Page English Abstract from OVID Search Results.

Schacht, J. (1999). Antioxidant therapy attenuates aminoglycoside-induced hearing loss. Ann. N. Y. Acad. Sci. 884, 125-30.

Scheibe, F., Haupt, H., Ising, H. (1999). Total magnesium concentrations of perilymph, cerebrospinal fluid and blood in guinea pigs fed different magnesium-containing diets. Eur. Arch. Otorhinolaryngol. 256, 215-9.

Scheibe, F., Haupt, H., Ising, H. (2000). Preventive effect of magnesium supplement on noise-induced hearing loss in the guinea pig. Eur. Arch. Otorhinolaryngol. 257, 10-16.

Scheibe, F., Haupt, H., Ising, H., Cherny, L. (2002). Therapeutic effect of parenteral magnesium on noise-induced hearing loss in the guinea pig. Magnes. Res. 15, 27-36.

Schneider, D., Schneider, L., Shulman, A., Claussen, C. F., Just, E., Koltchev, C., Kersebaum, M., Dehler, R., Goldstein, B., Claussen, E. (2000). Gingko biloba (Rokan) therapy in tinnitus patients and measurable interactions between tinnitus and vestibular disturbances. Int. Tinnitus J. 6, 56-62.

Seidman, M., Babu, S., Tang, W., Naem, E., Quirk, W. S. (2003). Effects of resveratrol on acoustic trauma. Otolaryngol. Head Neck Surg. 129, 463-70.

Seidman, M. D. (2000). Effects of dietary restriction and antioxidants on presbyacusis. Laryngoscope 110, 727-38.

Sha SH, Schacht J (1999) Salicylate attenuates gentamicin-induced ototoxicity. Lab Invest 79:807-813.

Shoji et al., "Differential Protective Effects of Neurotrophins in the Attenuation of Noise-Induced Hair Cell Loss", Hearing Research 146, 2000, pp. 134-142.

Song, B.-B., Sha, S. H., Schacht, J. (1998). Iron chelators protect from aminoglycosideinduced cochleo- and vestibulotoxicity in guinea pig. Free Radic. Biol. Med. 25, 189-195.

Takemura et al., "Direct Inner Ear Infusion of Dexamethasone Attenuates Noise-Induced Trauma in Guinea Pig", Hearing Research 196, 2004, pp. 58-68.

Takumida, M., Anniko, M., Ohtani, M. (2003). Radical scavengers for Meniere's disease after failure of conventional therapy: a pilot study. Acta Otolaryngol. (Stockh). 123, 697-703.

Tanswell AK, Freeman BA (1995) Antioxidant therapy in critical care medicine. New Horizons 3:330-341. One page abstract from OVID:Search Results on Apr. 22, 2006.

Teranishi, M., Nakashima, T., Wakabayashi, T. (2001). Effects of alpha-tocopherol on cisplatin-induced ototoxicity in guinea pigs. Hear. Res. 151, 61-70.

The Alpha-Tocopherol, Beta Carotene Cancer Prevention Study Group. (1994). The effect of vitamin E and beta carotene on the incidence of lung cancer and other cancers in male smokers. N. Engl. J. Med. 330, 1029-1035.

Usami, S., Hjelle, O. P., Ottersen, O. P. (1996). Differential cellular distribution of glutathione—an endogenous antioxidant—in the guinea pig inner ear. Brain Res. 743, 337-40.

Watanabe, K. Inai, S., Hess, A. Michel, O., Yagi, T. (2004). Acoustic stimulation promotes the expression of inducible nitric oxide synthase in the vestibule of guinea pigs. Acta Otolaryngol. Suppl. 553: (Stockh). 54-57.

Weijl, N. I., Elsendoorn, T. J., Lentjes, E. G., Hopman, G. D., Wipkink-Bakker, A., Zwinderman, A. H., Cleton, F. J., Osanto, S. (2004). Supplementation with antioxidant micronutrients and chemotherapy-induced toxicity in cancer patients treated with cisplatin-based chemotherapy: a randomised, double-blind, placebo-controlled study. Eur. J. Cancer 40, 1713-1723.

Yamashita, D., Jiang, H.-Y., Le Prell, C. G., Schacht, J., Miller, J. M. (2005). Post-exposure treatment attenuates noise-induced hearing loss. Neuroscience, 134, 633-642.

Yamashita D, Jiang HY, Schacht J, Miller JM (2004) Delayed production of free radicals following noise exposure. Brain Res 1019: 201-209.

Yamasoba et al., "Attenuation of Cochlear Damage From Noise Trauma by an Iron Chelator, a Free Radical Scavenger and Glial Cell Line-Derived Neurotrophic Factor in Vivo", Brain Research 815, 1999, pp. 317-325.

Yamasoba, T., Nuttall, A. L., Harris, C., Raphael, Y., Miller, J. M. (1998). Role of glutathione in protection against noise-induced hearing loss. Brain Res. 784, 82-90.

http://www.menieres.org/forums/NonCGI/Forum1/HTML/003686.html Constricted Blood Vessels, 1 Page.

International Search Report, International Application No. PCT/US 07/01422, Mar. 4, 2008, 2 pages.

* cited by examiner

COMPOSITION AND METHOD OF TREATING HEARING LOSS

RELATED APPLICATIONS

This patent application is a divisional of U.S. patent application Ser. No. 11/384,579, which was filed on Mar. 20, 2006 now U.S. Pat. No. 7,786,100.

GOVERNMENT LICENSE RIGHTS

This invention was made with government support under grant number DC04058 awarded by National Institute of Health National Institute of Deafness and Other Communication Disorders (NIH-NIDCD). The government has certain rights in the invention.

BACKGROUND OF THE INVENTION

1. Field of the Invention

The present invention generally relates to a composition for treating hearing loss. More specifically, the present invention relates to a composition for treating hearing loss that includes components that function through different biological mechanisms and provide an additive effect that is greater than the effect of the most effective of the individual components alone, and a method of treating hearing loss including the step of administering the composition to a mammal prior to or within 3 days following trauma to the inner ear.

2. Description of the Related Art

Extensive studies have been performed on compositions for treating hearing loss, along with methods of treating hearing loss using various compositions. In particular, antioxidants, among numerous other components, have been found to play a role in the prevention of noise-induced hearing loss. Specific antioxidants shown to be partially effective in reducing noise-induced hearing loss in animal models include glutathione (GSH)/glutathione monoethyl ester, N-acetylcysteine (NAC), resveratrol, allopurinol, R-phenylisopropyladenosine, salicylates, and vitamins A, C, and E. Otoprotective effects of the above individual dietary antioxidants are well known in the art.

Figure 1:
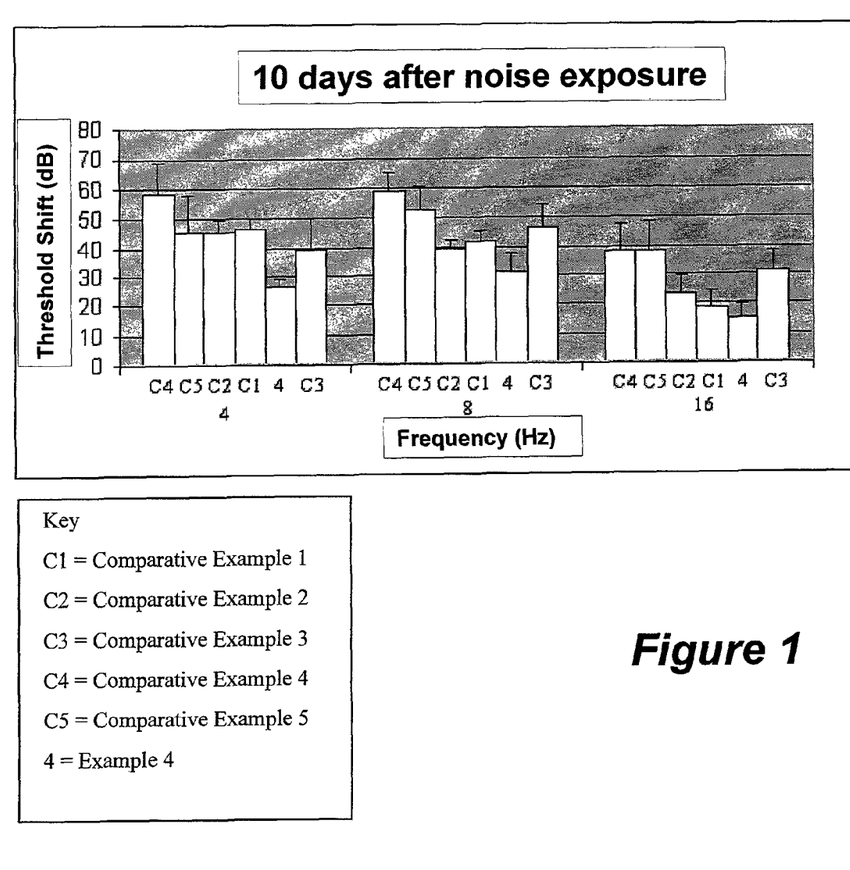
FIG. 1 is a graph showing the effect of treating hearing loss with Trolox® (a water-soluble analogue of alpha tocopheral) alone (Comparative Example 1, treatment started 3 days pre-trauma), sodium salicylate alone (Comparative Example 2, treatment started 3 days pre-trauma), Trolox® and vitamins A and C (Comparative Example 3, treatment started 1 hour pre-trauma), or a combination of Trolox® and salicylate (Example 4, treatment started 3 days post-trauma) on average reduction of a threshold shift in guinea pigs from baseline threshold sensitivity at 4, 8, and 16 kHz after exposure to 120 decibel SPL Octave Band Noise centered at 4 kHz for five hours.

To date, little, if any, additive effects have been found to exist by combining many of the known components for treating hearing loss. Additive effects, as used herein, refer to effects that are greater than the most effective of the individual components alone. For the most part, no greater effect is observed by combining many of the different components that are effective in treating hearing loss than the effect of the most effective individual component in the composition, i.e., combinations of agents are only as effective as the most effective single agent delivered alone. For example, FIG. 1 shows the results of experimentation relative to additive effects of Trolox®, which is a water-soluble analogue of alpha-tocopheral (vitamin E), in combination with vitamins A and C, as compared to the effects of Trolox® alone. The experimental conditions are described in further detail in the Examples section below. As is evident from FIG. 1, the combined effect of Trolox® and vitamins A and C in minimizing threshold shift, i.e., hearing loss, is no greater than the effect of Trolox® alone. As such, the combination of Trolox® and vitamins A and C does not produce an additive effect in treating hearing loss.

As the understanding of the mechanisms by which the various antioxidants work to treat or prevent hearing loss has become clearer, it has been found that combinations of certain antioxidants that act via complementary, but different, biochemical mechanisms may be more effective than the individual antioxidants alone. However, given the volume and variety of components that are known to affect hearing loss, as well as lack of knowledge relative to specific mechanisms by which the components function, additive effects between components have not been recognized to date. Further, significant treatments for preventing hearing loss, specifically noise-induced hearing loss, using a post-trauma treatment paradigm have yet to be achieved. There has been a long-felt need for such a treatment, since the vast majority of treatments to prevent noise-induced hearing loss are needed post-trauma.

In spite of the fact that additive effects between various components have not been recognized to date, certain disclosures have been made that generally group together many components for treating hearing loss. These disclosures do not teach with sufficient specificity combinations of specific components that exhibit additive effects in treating hearing loss or which are effective in post-trauma treatment paradigms. For example, U.S. Pat. No. 6,093,417 is directed to a composition to treat ear disorders. The composition is topically applied into an ear canal to treat the hearing disorder. Although the U.S. Pat. No. 6,093,417 is directed to a composition that may include many components that are known to be somewhat effective in reducing hearing loss alone, including vitamin E and zinc salts, such as zinc salicylate, there is no recognition of an additive effect between any of the components, when applied topically. As is evident from FIG. 1, many combinations of components do not exhibit additive effects. As such, the random combination of agents disclosed in the U.S. Pat. No. 6,093,417 would not provide any greater effect for treating hearing loss if included in the composition. Furthermore, effectiveness of the individual components greatly varies between oral, intravenous, and topical administration, and compositions for treating hearing loss are formulated differently depending on the contemplated mode of administration. Finally, the U.S. Pat. No. 6,093,417 does not teach with sufficient specificity biologically effective amounts of each component that would be sufficient to produce an effect individually, let alone additive effects between the various components. Thus, the disclosure of the U.S. Pat. No. 6,093,417 patent provides no further teaching than what was already known about each of the components, i.e., that each component, when used individually, is modestly effective in preventing hearing loss.

The use of vitamin E alone, in biologically effective amounts, has been disclosed for treating noise-induced hearing loss. More specifically, Hou et al., *Effects of alpha-tocopheral on noise-induced hearing loss in guinea pigs*, Hear Res. 179:1-8 (2003), discloses treatment of acoustical overstimulation with 10 to 50 mg/kg of alpha tocopheral. Further, the use of salicylates, in biologically effective amounts, has also been disclosed for treating hearing loss. More specifically, Kopke et al., *Reduction of noise-induced hearing loss using L-NAC and salicylate in the chinchilla*, Hear Res. 149: 138-146 (2000), discloses treatment of noise-induced hearing loss with 50 mg/kg of salicylate twice daily. However, none of the prior art suggests combining vitamin E or a salicylate in biologically effective amounts, and none of the prior art recognizes any type of additive effect that may be achieved with such a combination, or an ability to administer a combination of vitamin E and a salicylate post-trauma with excellent results for which, as set forth above, there has been a long-felt need. Furthermore, the fact that other similar combinations of components do not produce an additive effect, as shown in FIG. 1, illustrates that such additive effects would not be expected.

Although many of the components that are used to treat or prevent hearing loss provide other beneficial functions and are included in multivitamins, known multivitamins likewise do not include salicylates or biologically effective amounts of the components sufficient to treat or prevent hearing loss. Furthermore, multivitamins are generally used as part of a regular dietary regimen and there is no data that suggests the use of multivitamins that include a specific combination and concentration of components to prevent hearing loss induced by noise or other stress.

Thus, there is an opportunity to provide a composition and a method of treating hearing loss including the step of administering the composition that includes a specific combination of components having an additive effect that is greater than the effect of the most effective of the individual components alone in treating hearing loss when used in biologically effective amounts, and that is effective even when first administered as late as 3 days post-trauma.

SUMMARY OF THE INVENTION AND ADVANTAGES

The subject invention provides a composition for treating hearing loss including components that function through different biological mechanisms to provide an additive effect that is greater than the effect of the most effective of the individual components alone. The composition includes a biologically effective amount of a scavenger of peroxyl radicals for inhibiting propagation of lipid peroxidation that contributes to hearing loss. The composition also includes a biologically effective amount of a salicylate, which is a scavenger of hydroxyl radicals.

The subject invention also provides a method of treating hearing loss. The method includes the step of internally administering the composition of the subject invention including a biologically effective amount of each component to a mammal within three days of trauma to a middle or inner ear of the mammal.

The combination of the scavenger of peroxyl radicals and the salicylate, in the biologically effective amounts, provides an additive effect in treating hearing loss that is greater than the effects of the most effective of the individual components alone. Even more, the composition of the subject invention is effective in treating hearing loss even when administered as late as three days after trauma to the middle or inner ear of the mammal. As a result, the composition and method of treating hearing loss of the subject invention provide great promise in helping to minimize hearing loss resulting from trauma to middle or inner ears of mammals. Given the high incidence of noise-induced hearing loss in the general population worldwide, there has been a long-felt need for the composition and method of treating hearing loss of the subject invention in order to minimize socioeconomic effects that persist due to noise-induced hearing loss.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE PREFERRED EMBODIMENT

A composition for treating hearing loss includes components that function through different biological mechanisms to provide an additive effect that is greater than the effect of the most effective of the individual components alone. The composition is typically used for treating hearing loss resulting from trauma to a middle or inner ear of a mammal. The trauma may be further defined as mechanically-induced metabolic trauma, mechanical/metabolic trauma, stress trauma, stress-induced damage, or environmental stress. However, it is also possible that the composition may also be used to treat or prevent other types of hearing loss, including, for example, age-related hearing loss, antibiotic-induced hearing loss, and chemotherapeutic-induced hearing loss. The composition may further be used to prevent hearing loss during restoration surgery performed on the middle or inner ear.

It has been found that one result of noise trauma, or other stressors such as age and drugs as listed above, is that free radicals form in association with metabolic trauma. The free radicals damage sensitive structures, such as hair cells, within the ear. Vasoconstriction also occurs as a result of the noise, which leads to decreased blood flow to the middle and inner ear and causes cell death that results in hearing loss. It has been found that the underlying cause of vasoconstriction is noise-induced free radical formation. Specifically, one of the molecules formed in the inner ear as a result of the presence of free radicals is 8-isoprostane-2F alpha, which is a bioactive agent. The bioactive agent induces a constriction of blood vessels in the inner ear, which causes a reduction in blood flow. In order to counteract the free radical formation and the vasoconstriction, the composition of the subject invention includes a salicylate and a scavenger of peroxyl radicals. Unexpectedly, it was found that the composition including the combination of the scavenger of peroxyl radicals and the salicylate, in biologically effective amounts to be described in further detail below, produce the additive effect that is greater than the effect of any one of those components alone and, in some instances, greater than a sum of the effects of each of the components alone.

Antioxidants act through a variety of mechanisms. The scavenger of peroxyl radicals and the salicylate are members of two different classes of antioxidants that act through different mechanisms. Salicylates are scavengers of hydroxyl radicals and reduce free radicals (reactive oxygen species) that contribute to hearing loss. Scavengers of peroxyl radicals reduce reactive nitrogen species that also contribute to hearing loss. The scavengers of peroxyl radicals inhibit peroxynitrite-mediated tyrosine and guanine nitrosylation and minimize tissue damage induced by peroxynitrite, which is a reaction product of nitric oxide and the superoxide anion. Nitric oxide is widely implicated in pathological processes in the cochlea, including noise and ototoxic stress. The unexpected synergistic effects of these agents may be accounted for by the fact that they scavenge both reactive oxygen species and reactive nitrogen species; however, as shown in FIG. 1, the combination of vitamin E, i.e., the scavenger of peroxyl radicals, with vitamins A and C, which are other scavengers of hydroxyl radicals and are different from salicylates, is not as effective as the combination of vitamin E plus salicylate.

The salicylate may be selected from the group of salicylic acid, salts of salicylic acid, and combinations thereof. One specific example of a salicylate that may be suitable for purposes of the present invention is sodium salicylate. Salicylates are known in the art as scavengers of hydroxyl radicals. It is also known that salicylates can affect activation of the transcription factor nuclear factor-κB, thereby intervening in apoptotic pathways, and protect against drug-induced cell death in the cochlea.

The salicylate is present in the composition in a biologically effective amount. For purposes of the subject invention, the biologically effective amount is further defined as an amount that is sufficient to produce an additive effect in reduction in threshold shift when used in combination with the scavenger of peroxyl radicals. Additive effect, as used herein, refers to an effect that is greater than the effect of the most effective of the individual components alone. In order to produce the additive effect, the salicylate is typically present in the composition in a total amount of at least 3.2 international units (IU), more preferably from 3.2 IU to 29.0 IU, most preferably about 3.8 IU for an adult dosage, with the composition typically administered twice daily. Alternatively, the above dosages may be doubled and may be administered once daily. As known in the art, a conversion of IU to weight (mg/L, mmol/L) for salicylate is 0.00724 IU. Thus, at least 3.2 IU of sodium salicylate is equivalent to at least 442.5 mg of sodium salicylate, from 3.2 to 29.0 IU of sodium salicylate is equivalent to from 442.5 to 4000 mg sodium salicylate, and 3.8 IU of sodium salicylate is equivalent to 525 mg sodium salicylate. Specific amounts of the salicylate present in the composition may be dependent on the body weight of the mammal. In one specific example, the amount of salicylate present in the composition is about 7.5 mg/kg body weight. Thus, for an average human weighing about 70 kg, the amount of salicylate present in the composition may be about 525 mg.

The scavenger of peroxyl radicals inhibits propagation of lipid peroxidation and tissue damage induced by peroxynitrite, pathological processes that contribute to hearing loss. More specifically, the scavenger of peroxyl radicals serves a chain-breaking function to inhibit propagation of lipid peroxidation. As evident from the chain-breaking function of the scavenger of peroxyl radicals in lipid peroxidation, the scavenger of peroxyl radicals functions within cell membranes. A specific scavenger of peroxyl radicals that is contemplated for use in the composition of the subject invention is vitamin E. Vitamin E is a generic term for all tocols and tocotrienol derivatives with a biological activity of alpha-tocopherol. Primary dietary forms of vitamin E include vitamin E itself and alpha-tocopherol. Trolox®, a water-soluble analogue of alpha-tocopherol that is commercially available from Hoffman-Laroche, Ltd. of Basel, Switzerland, is another form of vitamin E with biological activity.

The scavenger of peroxyl radicals is typically present in the composition in an amount of at least 60 IU, more preferably from 60 IU to 540 IU, most preferably from 300 IU to 540 IU. For example, when the scavenger of peroxyl radicals is vitamin E, a conversion of IU to weight for vitamin E is 0.66 mg/IU, as known in the art. Thus, when the scavenger of peroxyl radicals is vitamin E, at least 60 IU of vitamin E is equivalent to at least 40 mg of vitamin E, from 60 to 540 IU of vitamin E is equivalent to from 40 to 357 mg vitamin E, and from 300 to 540 IU vitamin E is equivalent to from 200 to 357 mg vitamin E. As with salicylate, specific amounts of the vitamin E present in the composition may be dependent on the body weight of the mammal. In one specific example, the amount of vitamin E present in the composition is about 5.0 mg/kg body weight. Thus, for an average human weighing about 70 kg, the amount of vitamin E present in the composition may be about 350 mg.

Although salicylates and the scavenger of peroxyl radicals are known in the art for individually treating hearing loss, the combination of the salicylate and the scavenger of peroxyl radicals, more specifically the combination of salicylate and the vitamin E, exhibits an unexpected additive effect when combined in the biologically effective amounts. The additive effect for treating hearing loss is greater than the most efficacious of either the salicylate or the scavenger of peroxyl radicals alone. In some instances, the combination of the salicylate and the scavenger of peroxyl radicals is greater than the sum of the effects of the salicylate and the scavenger of peroxyl radicals alone. Such effects are not observed with combinations of other components, such as vitamins A, E and C, as is evident from FIG. 1. Specific effects of the composition of the subject invention on treating hearing loss are described in further detail below.

Amounts of the typical components included in the composition, along with more and most preferred amounts, are summarized in Table 1 below. As alluded to above, the composition is typically administered twice daily.

TABLE 1

| Component | Amount | More Preferred Amount | Most Preferred Amount | Typical Dosage, mg/kg body weight |
|---|---|---|---|---|
| Vitamin E | ≧60 IU | 60-540 IU | 300-540 IU | 5.0 mg/kg |
| Salicylate | ≧3.2 IU | 3.2-29.0 IU | 3.2-5.4 IU | 7.5 mg/kg |

Although no human experimentation has been performed to date, the amounts specified for the salicylate and the scavenger of peroxyl radicals correlate, in terms of biological effectiveness, to amounts used in animal studies on guinea pigs. Furthermore, it is to be appreciated that the biologically effective amounts of the salicylate and the scavenger of peroxyl radicals may be lower within the above ranges for persons of different body weight, as is evident from the typical dosages in Table 1 based on mg/kg.

In addition to the salicylate and the scavenger of peroxyl radicals, other components may also be present in the composition for treating hearing loss. For example, in one embodiment, the composition further includes a withanolide. Withanolides have been suggested for use in anti-inflammatory, anti-tumor, cytotoxic, and immunological applications. One example of a specific withanolide that may be included in the composition of the subject invention is the withanolide extracted from daylily plants. The extract is a powerful natural antioxidant, which may be effective in preventing cell death in the inner ear by interrupting the cell-death pathway initiated by deafferentation of the auditory nerve. When included in the composition, the withanolide may be present in an amount of at least 100 ppm, more preferably from 250 to 1000 ppm.

A method of treating hearing loss includes the step of internally administering the composition of the subject invention to a mammal, typically twice daily or at twice the preferred dose once daily, as set forth above. More specifically, the composition may be orally administered to the mammal, such as in the form of a tablet, liquid, gel, etc. Alternatively, the composition may be intravenously administered to the mammal through an IV or an injection of the composition. The composition may also be locally administered via the round window membrane of the cochlea. The salicylate, the scavenger of peroxyl radicals, and the other optional components, may be first combined to form the composition, with the composition then administered to the mammal. Alternatively, the salicylate, the scavenger of peroxyl radicals, and the optional components may be separately administered, in which case the composition forms within the mammal.

For purposes of the subject invention, hearing loss is objectively measured in terms of differences in threshold shift. In guinea pig studies, hearing loss and the efficacy of the composition of the subject invention for treating hearing loss is measured as an average difference in threshold shift from baseline threshold sensitivity at 4, 8, and 16 kHz, as compared to an untreated control, after exposure to 120 decibel SPL Octave Band Noise centered at 4 kHz for five hours. Larger differences in threshold shift correlate to less hearing loss and greater efficacy of the composition for treating hearing loss.

It is has been shown that hair cell loss correlates to threshold shift. For example, in guinea pig ears that recover from temporary threshold shift, morphological damage is limited to tips of stereocilia in a third row of outer hair cells (OHCs) whereas ears from animals with permanent threshold shift have damage to all three rows of OHCs and, in some cases, the inner hair cells (IHCs), with damage throughout the length of the stereocilia as well as the to the body of the hair cell.

The composition of the present invention is internally administered to the mammal, either orally or intravenously, within three days of trauma to a middle or inner ear of the mammal in order to alleviate permanent threshold shift. It is to be appreciated that by administrating the composition within three days of trauma, treatment prior to trauma is also contemplated through the method of the present invention. Data from animal studies indicate that temporary threshold shift measured 24 hours post-trauma is well-correlated with permanent threshold shift. Given the relationship between temporary threshold shift and permanent threshold shift, it is clinically beneficial to reduce temporary threshold shift. As such, the composition is preferably administered within one day of trauma to the middle or inner ear of the mammal. Even so, treatment within three days with the composition of the present invention is also effective in minimizing permanent threshold shift, as illustrated by Example 4 below.

Treatment within three days is most appropriate when the mammal has sustained trauma to the middle or inner ear through unexpected loud noise or other trauma. Ideally, the composition is administered to the mammal prior to trauma to the middle or inner ear. Treatment prior to trauma is most feasible when the mammal is preparing for sustaining trauma to the middle or inner ear. For example, the composition may be administered prior to restoration surgery performed on the middle or inner ear. As another example, if a person will be firing a weapon or attending an event such as a rock concert, the person may begin treatment prior to sustaining the trauma to the middle or inner ear to attain the best results.

After initial administration of the composition, the composition is typically administered to the mammal each day for at least five days following the trauma to the middle or inner ear of the mammal. Although excellent results have been achieved through such treatment, it is to be appreciated that other treatment regimens may also prove efficacious for purposes of the present invention.

As described in further detail in the Examples section below, an average difference in threshold shift in mammals from baseline threshold sensitivity at 4, 8, and 16 kHz, as compared to an untreated control, is at least 25 decibels after exposure to 120 decibel SPL Octave Band Noise centered at 4 kHz for five hours. More specifically, the threshold shift in mammals treated with the composition of the present invention is at least 25 decibels lower than the threshold shift in mammals that are treated with a control saline solution. To obtain those results, the composition is typically injected each day, twice a day, for three days prior to exposure to the noise and injected again each day for at least five days, typically up to ten days, subsequent to the exposure to the noise. The threshold shift is measured 10 days after exposure to the noise using auditory brainstem response (ABR) testing. Similar results would be anticipated using other alternative measures of auditory or sensory cell function, such as psychophysical tests or otoacoustic emission measures. Even when the composition is first administered as late as three days after exposure to the 120 decibel SPL Octave Band Noise centered at 4 kHz for five hours, an average difference in threshold shift in mammals from baseline threshold sensitivity at 4, 8, and 16 kHz, as compared to the untreated control, is at least 20 decibels.

In addition, outer hair cell loss and inner hair cell loss is measured both in the whole cochlea and in a trauma region of the cochlea. After treatment according to the method of the present invention, outer hair cell loss in the whole cochlea is less than 10%, as shown in FIG. 3, and inner hair cell loss in the whole cochlea is less than 5%. FIG. 4 shows the relative amounts of inner and outer hair cell loss for the various treatments set forth in FIG. 2. Although not specifically represented in the Figures, outer cell hair loss in the trauma region is less than 20%, while inner hair cell loss in the trauma region is less than 10%.

The following example, as presented herein, is intended to illustrate and not limit the invention.

EXAMPLES 1-4

The method of treating hearing loss with the composition of the present invention is performed on guinea pigs (NIH outbred strain, 250-350 grams) due to their extensive use in auditory research, including studies on noise-induced hearing loss, and because they provide a model similar to humans in terms of development. In order to determine efficacy of the composition of the present invention in treating hearing loss, baseline threshold sensitivity of the guinea pigs is measured binaurally using auditory brainstem response testing at 4, 8, and 16 kHz.

The guinea pigs are treated with vitamin E (Trolox®) and salicylate in the amounts shown in Table 2 twice per day. The amounts shown in Table 2 are 10 times expected human doses based on more rapid metabolism of guinea pigs relative to humans.

TABLE 2

| Component | Parts by Weight |
| --- | --- |
| Vitamin E (Trolox ®) | 50 mg/kg i.p. |
| Salicylate | 75 mg/kg s.c. |

For Example 1, the guinea pigs are first treated each day, twice a day, for three days prior to exposure to 120-dB SPL Octave Band Noise centered at 4 kHz for 5 hours. The noise causes trauma to middle or inner ears of the guinea pigs and is sufficient to cause permanent threshold shift, i.e., permanent hearing loss. The composition of the present invention is administered twice on the same day as the noise exposure, and twice each day for 10 days after the noise exposure. Ten days after the noise exposure, auditory sensitivity is measured using ABR. For Examples 2-4, a similar method of treatment is used, except treatment is started at different points in time relative to the noise exposure. For Example 2, the composition is first administered 1 hour after noise exposure, for Example 3, the composition is first administered 1 day after noise exposure, and for Example 4, the composition is first administered 3 days after noise exposure.

For ABR testing, the guinea pigs are anesthetized with 40 mg/kg ketamine and 10 mg/kg xylazine and placed on a warm heating pad in a sound attenuated chamber. ABR thresholds are determined at 4, 8 and 16 kHz frequencies. To test for the ABR thresholds, tone bursts 10 ms in duration (0.5 ms rise/fall) are presented at a rate of 17/sec. Up to 1024 responses are collected and averaged for each signal frequency to provide a measure of threshold shift at each frequency. Estimates of permanent hearing loss, shown in FIG. 2 in terms of threshold shift in decibels, are calculated as average threshold shift across ears and across frequencies.

After ABR testing, the guinea pigs are deeply anesthetized and decapitated. Temporal bones are quickly removed, dissected open and fixed with 4% paraformaldehyde. The following day, an otic capsule, lateral wall, and tectorial membrane are removed, and a bony modiolus is carefully detached. Organ of Corti tissue, attached to the modiolus, is permeabilized with 0.3% Triton-X and incubated with rhodamine phalloidin diluted 1:100 in phosphate buffered saline (30 min). After washing the tissues, individual turns from the organ of Corti are dissected, mounted on microscope slides, and examined and photographed using a Leica DMRB epiflourescence microscope. Hair cell counts are conducted, and cytocochleograms are prepared as known in the art. Referring to FIG. 3, percentages of missing outer hair cells (OHC) are determined based on the hair cell counts.

Comparative Examples 1-3

Guinea pigs are treated with 50 mg/kg of Trolox® alone, twice daily beginning 3 days pre-trauma (Comparative Example 1), 75 mg/kg of salicylate alone, twice daily beginning 3 days pre-trauma (Comparative Example 2), or a combination of 26 mg/kg Trolox®, 2.1 mg/kg vitamin A, and 71.4 mg/kg vitamin C (Comparative Example 3) once daily beginning 1 hour pre-trauma to illustrate that little or no additive effect is achieved with different combinations of components, other than the combination of the Trolox® and the salicylate. The results of treatment with Trolox® alone, the salicylate alone, or the combination of Trolox® and vitamins A and C are shown in FIG. 1. The guinea pigs are subjected to ABR testing, and the components of the ear are dissected, both as described above in the Example, to provide information on threshold shift and hair cell loss.

Comparative Examples 4-6

Guinea pigs are treated through other regimens in order to compare the efficacy of the composition of the present invention with the other compositions. For example, guinea pigs are separately treated in the same way as specified above in the Example with the following: no treatment (Comparative Example 4), a saline (NaCl) composition as a control (Comparative Example 5) administered each day, twice a day, for three days prior to exposure, or treatment with the composition used in Examples 1-4, but with treatment not starting until 5 days post-trauma (Comparative Example 6). The guinea pigs are subjected to the same ABR testing, and the components of the ear are dissected, as described above in the Example to provide information on threshold shift and hair cell loss. Threshold shift and hair cell loss resulting from treatment with the other compositions are shown in FIGS. 2 and 3.

Results

Figure 2:
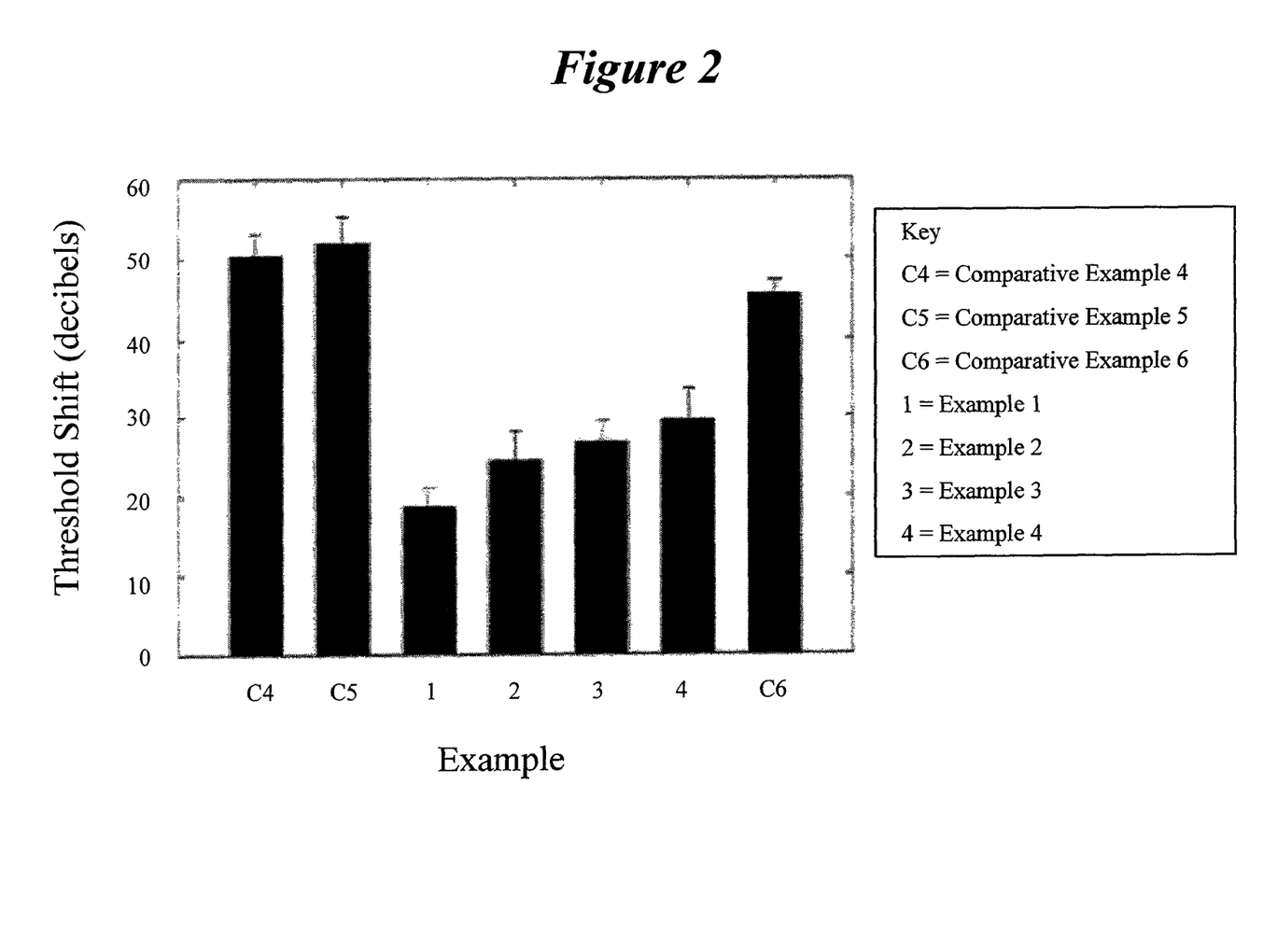
FIG. 2 is a graph showing the effect of treatment with a composition of the subject invention including Trolox® and sodium salicylate, in biologically effective amounts, after starting treatment 3 days pre-trauma (Example 1), 1 hour post-trauma (Example 2), 1 day post-trauma (Example 3), and 3 days post-trauma (Example 4), and Comparative Examples of an untreated control (Comparative Example 4), a saline-treated control (Comparative Example 5), and the composition of the present invention including vitamin E and the salicylate starting 5 days post-trauma (Comparative Example 6), on average reduction of a threshold shift in guinea pigs from baseline threshold sensitivity at 4, 8, and 16 kHz after exposure to 120 decibel SPL Octave Band Noise centered at 4 kHz for five hours.
Figure 3:
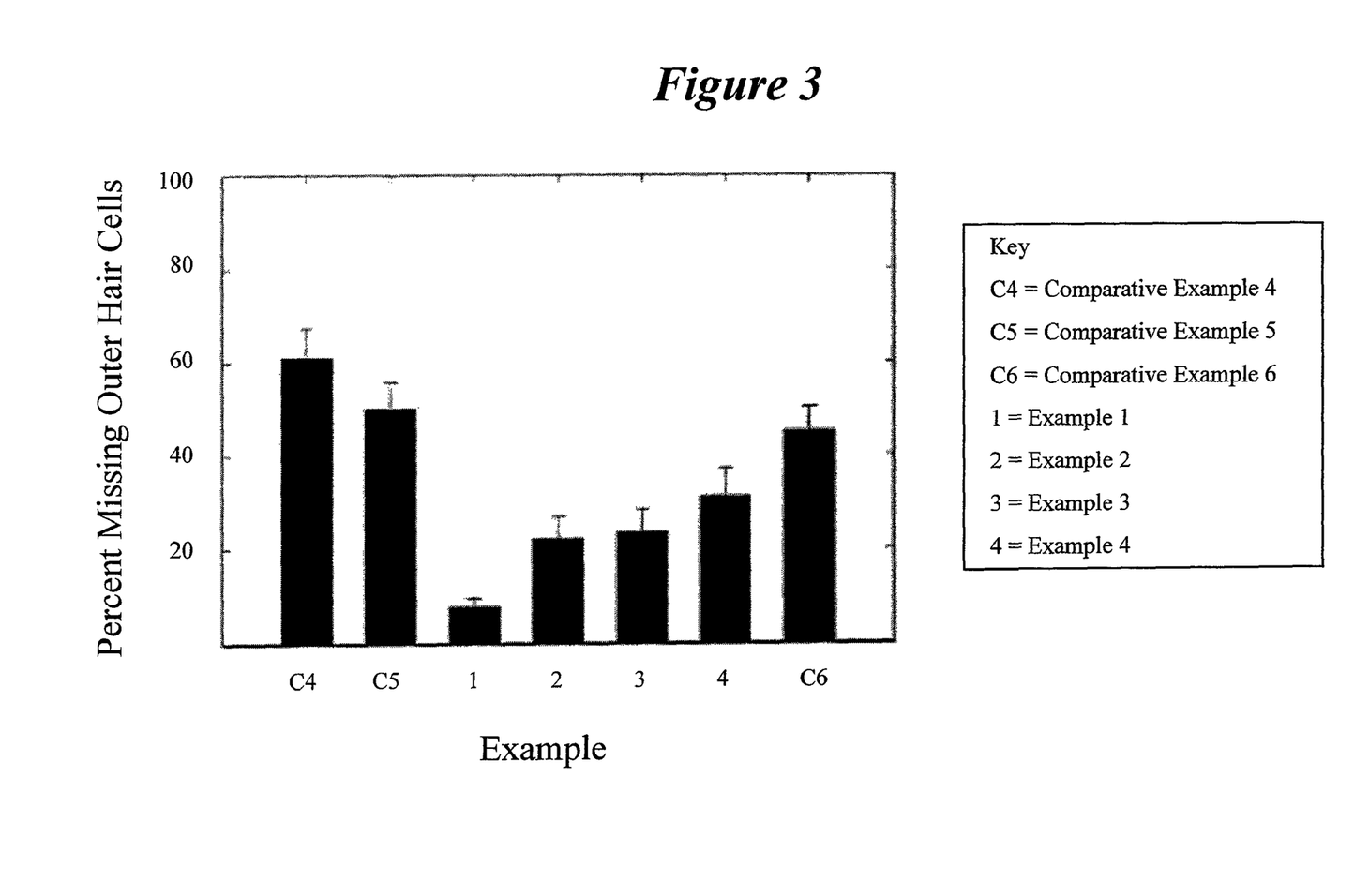
FIG. 3 is a graph showing corresponding amounts of missing outer hair cells in the region of the cochlea spanning 10-16 mm from the apex after the noise exposure specified above for FIG. 2 for each of the Examples and Comparative Examples of FIG. 2.
Figure 4:
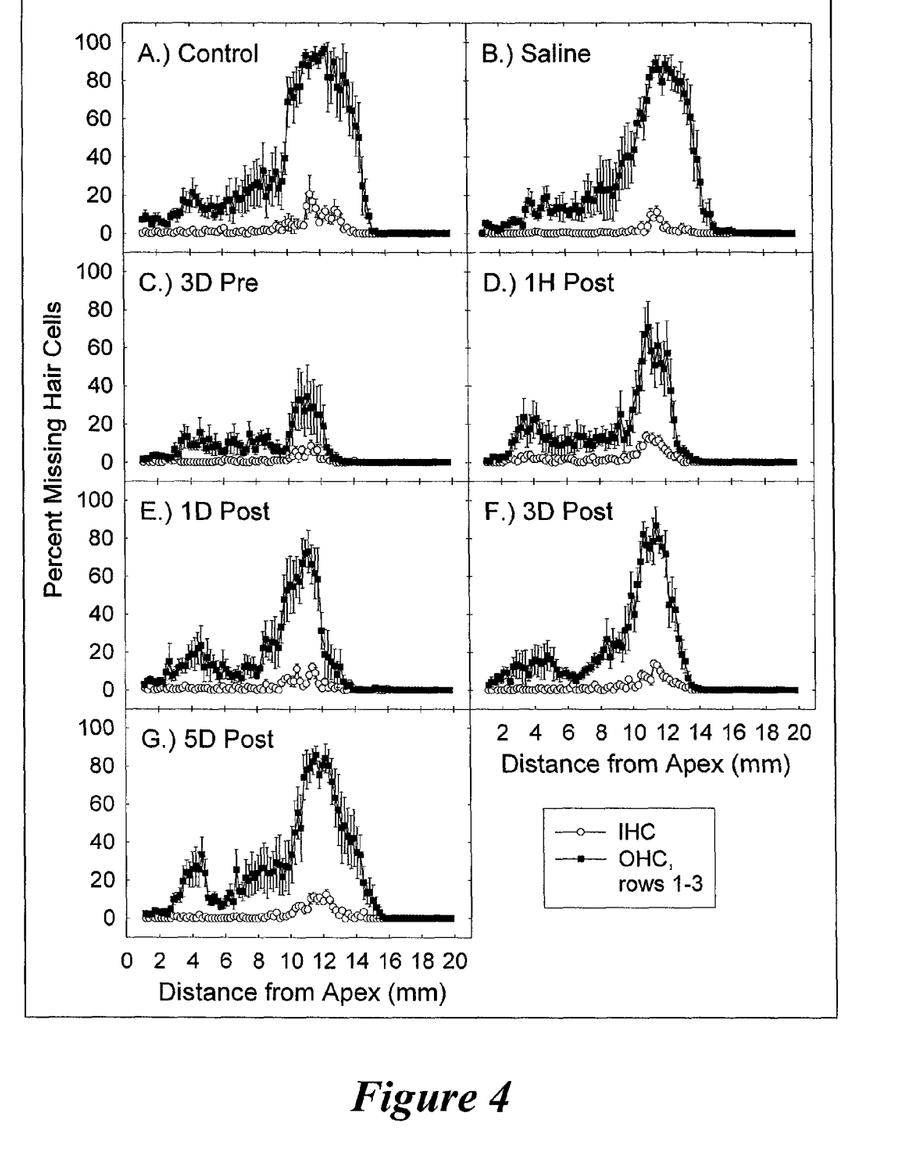
FIG. 4 is a series of graphs showing actual outer hair cell (OHC) loss and inner hair cell (IHC) loss with different treatment regimens.

Referring to FIGS. 2-3, the effect in treating hearing loss with composition of the present invention including Trolox® and the salicylate, in the biologically effective amounts, is clearly greater than that associated with the effectiveness of an untreated control (Comparative Example 1), a saline-treated control (Comparative Example 2), a combination of Trolox® and vitamins A and C (Comparative Example 3), Trolox® alone (Comparative Example 4), salicylate alone (Comparative Example 5), or the composition of Examples 1-4 with treatment starting 5 days post-trauma (Comparative Example 6). More specifically, noise exposure accompanied by treatment with the composition of the present invention within 3 days post-trauma results in a threshold shift of less than 30 decibels, as averaged across all frequencies, while noise exposure accompanied by treatment with a control substance results in a threshold shift of about 50. As such, a difference in threshold shift between treatment with the composition of the present invention and treatment with the control of saline solution is over 20 decibels. Consistent with the reduction in noise-induced hearing loss, hair cell counts revealed significantly reduced sensory cell death with the treatments used in Examples 1-4, with the greatest protection observed with treatment starting 3 days prior to exposure to the noise (Example 1). More specifically, less than 10% of outer hair cells in the whole cochlea are missing after treatment with the composition of the present invention 3 days pre-trauma (Example 1). However, even with treatment starting three days post treatment (Example 4), outer hair cell loss is about 30%, compared to about 60% outer hair cell loss for the untreated control (Comparative Example 1).

Furthermore, as shown in FIG. 1, the Comparative Examples in which Trolox® alone, the salicylate alone, or a combination of Trolox® and vitamins A and C are used clearly do not exhibit the same additive effect that is observed when Trolox® and the salicylate are used in combination, as shown in Examples 1-4 in FIGS. 1-3.

The invention has been described in an illustrative manner, and it is to be understood that the terminology which has been used is intended to be in the nature of words of description rather than of limitation. Obviously, many modifications and variations of the present invention are possible in light of the above teachings, and the invention may be practiced otherwise than as specifically described.

What is claimed is:

1. A composition for treating hearing loss including components that function through different biological mechanisms to provide an additive effect that is greater than the effect of the most effective of the individual components alone, said composition comprising:
   vitamin E present in an amount of from 60 IU to 540 IU for inhibiting propagation of lipid peroxidation that contributes to hearing loss; and
   a salicylate present in an amount of at least 3.2 IU for reducing hydroxyl radicals that also contribute to hearing loss.

2. A composition as set forth in claim 1 wherein said salicylate is further defined as sodium salicylate.

3. A composition as set forth in claim 1 wherein said vitamin E is further defined as a water-soluble analogue of alpha tocopheral.

4. A composition as set forth in claim 1 further comprising a withanolide.

5. A composition as set forth in claim 1 that produces an average difference in threshold shift in mammals from baseline threshold sensitivity at 4, 8, and 16 kHz of at least 25 decibels after exposure to 120 decibel SPL Octave Band Noise centered at 4 kHz for five hours, as compared to an untreated control.

6. A composition as set forth in claim 5 that produces an average difference in threshold shift in mammals from baseline threshold sensitivity at 4, 8, and 16 kHz of at least 20 decibels when first administered three days after exposure to 120 decibel SPL Octave Band Noise centered at 4 kHz for five hours, as compared to an untreated control.

7. A composition as set forth in claim 1 wherein the salicylate is present in the composition in an amount of from 3.2 IU to 29.0 IU.

* * * * *